United States Patent [19]

Bar-Shalom et al.

[11] Patent Number: 5,618,560
[45] Date of Patent: Apr. 8, 1997

[54] CONTROLLED RELEASE ERODIBLE COMPOSITION

[75] Inventors: Daniel Bar-Shalom, Kokkedal; Ture Kindt-Larsen, Vedbæk, both of Denmark

[73] Assignee: BM Research A/S, Vaerlose, Denmark

[21] Appl. No.: 470,828

[22] Filed: Jun. 6, 1995

Related U.S. Application Data

[63] Continuation of Ser. No. 469,446, filed as PCT/DK89/00068, Mar. 22, 1989, published as WO89/09066, Oct. 5, 1989, abandoned.

[30] Foreign Application Priority Data

Mar. 24, 1988 [WO] WIPO ............ PCT/DK88/00049
Oct. 31, 1988 [DK] Denmark ............ 6062188

[51] Int. Cl.⁶ .......... A61K 9/10; A61K 9/24; A61K 9/26; A61K 47/34
[52] U.S. Cl. .......... 424/486; 424/426; 424/471; 424/472; 424/473; 514/960; 514/975
[58] Field of Search .......... 424/484, 486, 424/426

[56] References Cited

U.S. PATENT DOCUMENTS

| | | | |
|---|---|---|---|
| 3,594,469 | 7/1971 | Whitehead et al. | 424/22 |
| 3,634,584 | 1/1972 | Pole | 424/21 |
| 4,053,581 | 10/1977 | Chien et al. | 424/15 |
| 4,230,686 | 10/1980 | Schopflin et al. | 424/22 |
| 4,343,789 | 8/1982 | Kawata et al. | 424/78 |
| 4,351,825 | 9/1982 | Sothmann et al. | 424/19 |
| 4,368,185 | 1/1983 | Mizuno et al. | 424/436 |

(List continued on next page.)

FOREIGN PATENT DOCUMENTS

| | | |
|---|---|---|
| 104696 | 9/1966 | Denmark . |
| 197/82 | 4/1982 | Denmark . |
| 2362/85 | 8/1987 | Denmark . |
| 052916 | 6/1982 | European Pat. Off. . |
| 025697 | 6/1983 | European Pat. Off. . |
| 0132384 | 1/1985 | European Pat. Off. . |

(List continued on next page.)

OTHER PUBLICATIONS

Tuda, et al. Basic Course for Medical Development XI—A Method of Drug Preparation (1st. vol), 1971 pp. 134–139.
Huttenrauch, R., "Fortschritte and Tendenzen in der Entwicklung neuer Arzneiformen", *Die Pharmazie*, 33: 481–499 (1978) (No Translation).
Hsieh, et al, "Enhanced release of drugs from silicone elastomers (II): Induction of Swelling and Changes in Microstructure", *Drug Develop. Industr. Pharm.*, 11: 1411–1432 (1985).
Carelli, et al, "Factors in zero-order release of clonidine hydrochloride from monolithic poly–dimethyl silozane matrices", *Int.J.Pharm*, 35:21–8, 1987 (Chem.Abs., 106:14389j (1987).

*Primary Examiner*—Edward J. Webman
*Attorney, Agent, or Firm*—Foley & Lardner

[57] ABSTRACT

Articles for the controlled delivery of an active substance into an aqueous phase by erosion of surfaces of the articles at a substantially constant and pH-independent rate, the articles comprising a matrix of crystalline polyethylene glycol polymer and a non-ionic emulsifier having an HLB value in the range of from about 4 to about 16 dispersed in the matrix in an amount of between about 2% and 50% by weight of the crystalline polyethylene glycol polymer and the emulsifier, the emulsifier having at least one domain which enables the emulsifier to become emulsified in the melted crystalline polyethylene glycol polymer and being selected from the group consisting of a fatty acid ester and a fatty alcohol ether, the active substance being dispersed in the matrix or located in geometrically well-defined zones within the crystalline PEG phase or dispersed in the emulsifier and, optionally, a filler. The non-ionic emulsifier or the active substance substantially eliminates water diffusion in the interface between the polymer crystals to thereby act as a repair medium and maintain substantially the geometric shape of the articles and, thus, maintain substantially constant the surface area exposed to solution.

60 Claims, 2 Drawing Sheets

U.S. PATENT DOCUMENTS

| | | | |
|---|---|---|---|
| 4,629,621 | 12/1986 | Snipes | 424/19 |
| 4,690,824 | 9/1987 | Powell et al. | 424/468 |
| 4,744,976 | 5/1988 | Snipes et al. | 424/408 |
| 4,764,378 | 8/1988 | Keith et al. | 424/486 |
| 4,774,074 | 9/1988 | Snipes | 424/19 |
| 4,784,855 | 11/1988 | Yamashita et al. | 424/422 |
| 4,806,337 | 2/1989 | Snipes et al. | 71/65 |
| 5,244,668 | 9/1993 | Snipes | 424/486 |

FOREIGN PATENT DOCUMENTS

| | | |
|---|---|---|
| 186019 | 7/1986 | European Pat. Off. . |
| 214735 | 7/1986 | European Pat. Off. . |
| 232877 | 8/1987 | European Pat. Off. . |
| 230654 | 8/1987 | European Pat. Off. . |
| 246819 | 11/1987 | European Pat. Off. . |
| 281236 | 9/1988 | European Pat. Off. . |
| 434013 | 4/1980 | Sweden . |
| 2160100 | 12/1985 | United Kingdom . |

CONTROLLED RELEASE ERODIBLE COMPOSITION

This application is a continuation of application Ser. No. 07/469,446, filed as PCT/DK89/00068, Mar. 22, 1989, published as WO89/09066, Oct. 5, 1989, now abandoned.

FIELD OF INVENTION

The present invention relates to a composition for controlled delivery of an active substance into an aqueous phase.

BACKGROUND OF THE INVENTION

It is known to obtain sustained release of an active substance, e.g. a pharmaceutically active powder, by embedding it in a matrix of an insoluble substance from which the active substance will gradually diffuse. Sustained release of an active substance contained in a tablet core may also be achieved by applying to the core a semipermeable coating through which water and dissolved active substance may diffuse or an insoluble coating provided with a hole through which the active substance is released. Gradual release of an active substance may furthermore be obtained by microencapsulating particles of an active substance in one or more layers of film which may be of different types, e.g. of a type which mediates diffusion of the active substance or release thereof in the intestines.

These conventional ways of providing sustained release of an active substance have certain drawbacks, in that it is difficult to maintain a constant concentration of the active substance, for example a constant concentration of a pharmaceutically active substance in plasma for the entire period when the dosage form is present in the body. In particular, this may be the problem with drugs which have a brief half-life in the body. Furthermore, the penetration of water through diffusion coatings may cause hydrolysis of active substances which are unstable in an aqueous environment.

The purpose of the present invention is to overcome these drawbacks by providing a composition from which release of an active substance is strictly controlled and which prevents degradation of the active substance by hydrolysis until the time of release.

SUMMARY OF THE INVENTION

Accordingly, in one embodiment, the present invention relates to a composition for controlled delivery of an active substance into an aqueous phase by erosion at a substantially constant rate of a surface or surfaces of the composition, the composition comprising a matrix of a substantially water soluble crystalline polymer or a mixture of substantially water soluble crystalline polymers, a surface active agent or a mixture of surface active agents dispersed in the crystalline polymer phase in an amount of 0–50% by weight of the crystalline polymer and surface active agent, the surface active agent comprising a compound or compounds having at least one domain which is compatible with the crystalline polymer phase and at least one other domain which is substantially lipophilic, and having a melting point which is lower than that of the crystalline polymer, at least one active substance substantially homogeneously dispersed in the crystalline polymer phase and/or dispersed in the surface active agent and/or located in geometrically well-defined zones within the composition, and optionally, a filler, the surface active agent and/or the active substance reducing the water affinity of domains between grains and in cracks in the crystalline polymer matrix and in the crystalline polymer matrix itself, thereby substantially eliminating water diffusion in the interface between the polymer crystals, so that the erosion is predominantly effected by the dissolving action of an aqueous medium on a surface or surfaces of the composition exposed to the medium.

The combination of the matrix and the active substance and/or the surface active agent must be substantially impenetrable to fluids of the aqueous phase, for example body fluids present where the composition of the invention is introduced into the body (e.g. in the gastrointestinal tract, including the rectum, in the vagina or subcutaneously) or into a body cavity via a catheter (e.g. the urinary bladder, the gall bladder, the uterus, a central nervous system cavity, infectious/malignant/post-operative cavities, etc.), in order to avoid degradation of The active substance residing in the matrix due to the action of water in the case of an active substance which is susceptible to hydrolysis. The inclusion of the active substance in a matrix into which water diffusion is substantially eliminated will thus impart stability to the composition, so that the active substance will remain active even when the composition has been exposed to body fluids or other fluids for the predetermined time. As the fluids can only act on the surface of a matrix of this type, the active substance embedded therein is only exposed to the fluids in question when it is released or immediately prior to its release from the matrix. A matrix of a type which is substantially impenetrable to water will therefore ensure the stability of the active substance in the matrix for the entire period of time when the composition is present in the aqueous phase, for example a body cavity, until the time when the active substance is released, and will also ensure a controlled and reproducible release rate of the active substance from the matrix, since the release proceeds gradually from the surface or surfaces of the matrix exposed to the fluids in question.

The rate at which the active substance is released from the matrix is a predetermined rate, i.e. a rate which is controllable over a certain period of time. The release rate required in each particular instance may inter alia depend on the amount of active substance to be released for it to exert the desired effect, as well as on the overall dosage of the active substance contained in the matrix. The substance of which the matrix is composed and the distribution of the active substance in the matrix may therefore be selected according to one or more of these criteria to ensure the desired level of release of the active substance.

The composition of the invention has the advantage that the dosage of the active substance included in the matrix may be measured so that an appropriate constant or pulsatile dosage thereof will be available in the aqueous phase for the entire period of time that the composition is present in the aqueous phase; the nature of the matrix structure, i.e. its water-impenetrability, prevents degradation by hydrolysis or other means of the active substance due to diffusion of water into the matrix even if the active substance in itself is unstable in an aqueous environment.

Due to the controlled release of the active substance obtainable from the composition of the invention, it is possible to obtain a substantially constant rate of release or a controlled pulsatile release of the active substance over a specific period of time, corresponding to the dosage necessary for the treatment in question, so that adherence to a strict dosage regimen, e.g. requiring administration of a drug at set intervals up to several times a day, may be dispensed with. Furthermore, it is possible to include two or more different active substances in the composition of the invention, adapted to be released at different concentrations and/or intervals, thus making it easier for patients to follow a prescribed regimen.

An additional advantage of the composition of the invention, compared to other known controlled release compositions, is that it may be produced by relatively simple and inexpensive methods, e.g. by extrusion, as will be explained in more detail below. Furthermore, the composition according to the invention allows for the incorporation of high concentrations of the active substance relative to the composition's size. This is obviously a great advantage, notably when the composition is to be used for the delivery of a pharmaceutically active substance, since it allows for the delivery of the required amount of the active substance without the composition being unneccesarily large. In addition, sparingly soluble or non-soluble active substances may be readily incorporated into the composition of the invention, since such substances are compatible with the lipophilic domains of the surface active agent. The composition of the invention may thus be used for the delivery of, for example, sparingly soluble or non-soluble pharmaceutical powders which can otherwise be difficult to administer.

Rather than comprising a water soluble crystalline polymer or mixture of such polymers, the matrix may comprise a substance which is nonsoluble in water, together with the active substance and a hydrophilic substance which is at least partly accessible to the fluids of the aqueous phase and which swells in the presence of said fluids, resulting in a localized disruption of the matrix in the vicinity of the hydrophilic substance and the release of the active substance.

The invention, in another embodiment, thus relates to a composition for controlled delivery of an active substance into an aqueous phase, the composition comprising a matrix of room-temperature vulcanizing rubber (RTV rubber) in which particles of a superabsorbent polymer are substantially homogeneously distributed, the superabsorbent polymer particles also being present substantially near the surface of the composition, and at least one active substance substantially homogeneously dispersed in the matrix and/or located in geometrically well-defined zones within the matrix, in which the liquid of the aqueous phase is able to diffuse into the surface of the matrix at a limited rate, resulting in swelling of the superabsorbent polymer particles and the localized disruption of the matrix in the vicinity of the swollen particles, whereby the active substance is released in a specifically controlled manner according to its distribution in the matrix.

DETAILED DISCLOSURE OF THE INVENTION

Figure 1:
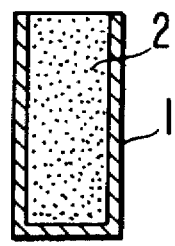
FIG. 1 shows a sectional side view of a coated cylinder rod-shaped composition for the constant released of an active substance.

In the first embodiment of the invention, i.e. when matrix of the composition comprises a substantially water soluble crystalline polymer or a mixture of substantially water soluble crystalline polymers, a surface active agent will typically be dispersed in the crystalline polymer phase.

The surface active agent comprises a compound or compounds having at least one domain which is compatible with the crystalline polymer phase and at least one other domain which is substantially lipophilic. The term "compatible", as used in the context of the invention, refers to the fact that the surface active agent is able to become emulsified in the melted polymer, as explained below. The surface active agent functions partly as a repair medium, in that it has a substantially hydrophilic domain which gives it affinity to the crystalline polymer phase, thereby filling in domains between grains and in cracks in the crystalline polymer matrix, and partly as a surfactant, in that the substantially lipophilic domains reduce the water affinity in the interfaces between the grains and in the cracks in the crystal structure, thereby substantially eliminating water diffusion in the interface between the polymer crystals.

The above-mentioned cracks and grains in the crystalline polymer matrix are a result of the process in which the crystals are formed. During the crystallization process the matrix shrinks and tends to form cracks and imperfect zones between the crystal grains. In order to retain its function as a repair medium, the surface active agent should be mobile after the polymer material of the matrix has solidified and the crystals have been formed. Therefore, the melting point of the surface active agent must be lower than that of the crystalline polymer phase.

In order for the surface active agent to function properly as a repair medium for the cracks and grains in the matrix, it is further necessary that a substantially homogenous distribution of the surface active agent can be obtained in the melted polymer prior to crystallization. Thus, the surface active agent must be capable of becoming emulsified in the melted polymer.

It has been found that substantially hydrophobic active substances tend to result in a decrease in the erosion rate of the composition. Substantially hydrophilic or water-soluble active substances have been shown to have the opposite effect, i.e. they tend to result in a faster erosion of the matrix. It has furthermore been found that if the composition is prepared without an active substance, the composition will tend to erode at a relatively fast rate.

The degree of dispersion of the surface active agent in the matrix seems to be important for the erosion rate of the matrix, a more uniform dispersion resulting in a slower erosion rate. It is thus believed that substantially hydrophobic active substances tend to lead to a more uniform dispersion of the surface active agent, thereby leading to a decreased erosion rate of the matrix, while nonhydrophobic active substances have the opposite effect.

When the composition is prepared with an active substance which is not substantially hydrophobic, or when the content of the active substance in the composition is relatively low, it may therefore be desirable to add one or more fillers in order to modify the dispersion of the surface active agent and reduce the erosion rate of the matrix. It is believed that the addition of a filler serves to increase the viscosity of the mixture, whereby the surface active agent becomes more uniformly dispersed in the matrix. Examples of suitable fillers are dextrin, sucralfate, calcium hydroxyl-apatite, calcium phosphate and fatty acid salts such as magnesium stearate. The filler may be added in an amount so that the combination of the filler and the active substance comprises up to about 60%, typically up to about 50%, by weight of the composition.

The surface active agent is typically a non-ionic emulsifier comprising one or more fatty acid esters and/or fatty acid ethers, for example a fatty acid ester and/or fatty acid ether having carbon chains of from 12 to 24 carbon atoms, typically from 12 to 20 carbon atoms, such as an ester and/or ether of palmitic acid or stearic acid. Typical surface active agents may comprise a polyglycol ester or ether, a polyethylene glycol ester or ether, a polyhydroxy ester or ether and/or a sugar ester or ether such as a sorbitan ester or ether. The surface active agent will suitably have an HLB (hydrophilic-lipophilic balance) value of from about 4 to about 16. Furthermore, the surface active agent is preferably an emulsifier which is approved for use in products to be ingested by humans or animals, i.e. pharmaceuticals and/or foodstuffs. A preferred surface active agent is polyethylene glycol monostearate, in particular polyethylene glycol 400 monostearate. Tartaric acid, citric acid and lactic acid esters of mono- and diglycerides, as well as fatty acid esters of glycerol, may also be employed as a surface active agent.

It may in certain cases be desirable to incorporate a mixture of surface active agents into the matrix, in order to improve the dispersion of the primary surface active agent in the matrix and reduce the erosion rate.

In some cases, the active substance itself will be capable of functioning as a surface active agent, i.e. it will have at least one domain which is compatible with the crystalline polymer phase and at least one other domain which is substantially lipophilic, so that the active substance alone will be capable of becoming substantially homogeneously dispersed in the crystalline polymer phase and substantially eliminating diffusion of water into the matrix. In this case, the role of the surface active agent, i.e. its function as a repair medium and as a surfactant, will be partially or completely fulfilled by the active substance itself, and little or no surface active agent may be required. Thus, when the active substance itself has properties of a non-ionic emulsifier, the surface active agent may be absent from the composition or may be present in the composition in an amount of, for example, about 0–2% by weight of the matrix.

When the active substance does not possess properties of a surface active agent, the surface active agent is typically present in the composition in an amount of about 2–50%, e.g. about 5–50%, typically about 10–40%, more typically about 15–35%, such as about 20–30%, by weight of the crystalline polymer and surface active agent. As mentioned above, a surface active agent content of less than 2% may however be employed when the active substance possesses surface active agent properties. On the other hand, a maximum surface active agent content of about 50%, depending on the nature of the surface active agent, the active substance and the crystalline polymer, as well as on the desired delivery characteristics of the composition, will be sufficient to ensure the required repair and surfactant effects. If the content of the surface active agent exceeds about 50%, there is a risk of phase inversion, whereby the surface active agent may become the continuous phase.

The crystalline polymer matrix typically comprises a polyglycol, e.g. in the form of a homopolymer and/or copolymer. Preferred polymers are polyethylene glycols or block copolymers of ethylene oxide and propylene oxide. Polyethylene glycols which are suitable for use in the crystalline polymer matrix are those having a molecular weight of from about 2000 to about 500,000 daltons, typically from about 5000 to about 100,000 daltons, more typically from about 10,000 to about 50,000 daltons, and especially from about 20,000 to about 35,000 daltons. A preferred polyethylene glycol is one which has a molecular weight of about 35,000 daltons. Typical block copolymers may be comprised of up to about 30% by weight of the polypropylene oxide based block, and have a molecular weight of above about 5000 daltons, typically about 5000 to about 30,000 daltons, more typically about 8000 to about 15,000 daltons.

The crystalline polymer matrix must have a melting point which is above the temperature of the aqueous medium in which the composition of the invention is to be used. Thus, the polymer(s) employed in the matrix will suitably have a melting point of about 20°–120° C., typically about 30°–100° C., more typically about 40°–80° C., depending on the how the composition is to be employed. In particular, when the composition of the invention is used for the delivery of a drug for human or veterinary use, the matrix will suitably have a melting point of about 40°–80° C.

The active substance to be delivered by the composition according to the invention can be a drug for human or veterinary use, a vitamin or other nutritional supplement, a disinfectant, a deodorant or another substance to be administered continuously in an aqueous environment.

The composition of the invention is especially suitable for the delivery of an active substance which is a pharmaceutically active substance, in particular a pharmaceutically active powder. The pharmaceutically active substance or substances included in the composition of the invention may be selected from many therapeutic categories, in particular from substances which may advantageously be administered orally, rectally, vaginally or subcutaneously, or administered to a body cavity (e.g. the urinary bladder, the gall bladder, the uterus, a central nervous system cavity, infectious/malignant/post-operative cavities, etc.). Examples of such substances are antimicrobial agents, analgesics, antiinflammatory agents, counterirritants, coagulation modifying agents, diuretics, sympathomimetics, anorexics, antacids and other gastrointestinal agents, antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, β-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable active substances may be selected from contraceptives and vitamins as well as micro- and macronutrients.

The composition is in addition suitable for the delivery of polypeptides, for example hormones such as growth hormones, enzymes such as lipases, proteases, carbohydrases, amylases, lactoferrin, lactoperoxidases, lysozymes, nanoparticles, etc., and antibodies. The composition may also be employed for the delivery of microorganisms, either living, attenuated or dead, for example bacteria, e.g. gastrointestinal bacteria such as streptococci, e.g. *S. faecium*, Bacillus spp. such as *B. subtilis* and *B. licheniformis*, lactobacteria, Aspercillus spp., bifidogenic factors, or viruses such as indigenous vira, enterovira, bacteriophages, e.g. as vaccines, and fungi such as baker's yeast, *Saccharomyces cerevisiae* and fungi imperfecti. The composition may also be used for the delivery of active agents in specialized carriers such as liposomes, cyclodextrines, nanoparticles, micelles and fats.

One of the uses for which the composition of the invention is well-suited is the delivery of antimicrobial agents to the vagina. Examples of such agents are antifungals, for example imidazole antifungals such as clotrimazole, econazol, ketoconazole and miconazole, polyene antifungal antibiotics such as nystatin, and antiprotozoais such as metronidazole and ornidazole.

A pharmaceutically active powder to be administered by the composition of the invention will suitably have a particle size of from about 0.1 μm to about 500 μm, typically from about 0.5 μm to about 300 μm, more typically from about 1 μm to about 200 μm, especially from about 5 μm to about 100 μm.

The active substance will suitably be present in an amount of up to about 60%, typically up to about 50%, by weight of the composition.

An active substance content of about 60% is contemplated to be the maximum content which still allows for a sufficient content of the crystalline polymer matrix and the surface active agent in the composition. The active substance may, on the other hand, be present in the composition in much smaller amounts, depending on the nature and strength of the active substance in question.

As mentioned above, the presence of the surface active agent and/or the active substance in the crystalline polymer matrix will reduce the water affinity of domains between grains and in cracks in the matrix, thereby substantially eliminating water diffusion in the interface between the polymer crystals, so that the erosion is predominantly effected by the dissolving action of an aqueous medium on a surface or surfaces of the composition exposed to the medium. Diffusion of water into the composition is thus substantially limited to the surface layer of the matrix, whereby the matrix is eroded at a substantially constant and pH-independent rate. As a result, a substantially zero order release of the active substance is obtained, the term "zero order" referring to the fact that the release rate of the active substance is substantially constant with time, when the active substance is substantially homogeneously distributed in the matrix. In the case of the active substance being located in geometrically well-defined zones within the matrix, the result of the constant erosion rate of the matrix will be a strictly controlled pulsatile release of the active ingredient.

The geometric form of the composition is important for the obtainment of the above-mentioned controlled zero order or pulsatile release. Thus, in a preferred version of the invention, the composition of the invention has a geometric shape which enables a substantially constant surface area to become exposed during erosion of the matrix. The composition may thus have the shape of a cylindrical rod which is provided with a coating which is substantially insoluble in and impermeable to fluids such as body fluids during the intended release period, the coating having an opening at one or both ends. Polymers useful as coatings are preferably those which are possible to process by extrusion, solution or in the form of a dispersion. Most preferred are those which are available in a food grade or pharmaceutical grade quality. Examples of such polymers are cellulose acetate, polyamide, polyethylene, polyethylene terephthalate, polypropylene, polyurethane, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA), styrene-butadiene-styrene (SBS) and styrene-isoprene-styrene (SIS).

The coating may further comprise any of the above-mentioned matrix materials in a form which erodes at a substantially slower rate than the rest of the matrix. The coating may thus comprise a matrix of one or more substantially water soluble crystalline polymers and a surface active agent, the coating being one which is eroded in the aqueous phase at a substantially slower rate that than the matrix material comprising the active substance, whereby a substantially constant area of the matrix comprising the active substance is exposed during erosion of the composition, and whereby the coating is substantially eroded upon erosion of the matrix comprising the active substance. Such a coating will be designed so that its longitudinal erosion rate is substantially the same as the longitudinal erosion rate of the matrix, whereby the matrix and the coating will erode longitudinally towards the center of the composition at substantially the same rate. Thus, when the matrix has been completely eroded by the aqueous medium, the coating will also be substantially completely eroded. A composition having such a coating has the obvious advantage of being completely biodegraded upon release of the active substance. Such a coating will typically be a combination of a polyethylene glycol and a mixture of, for example, polyethylene glycol 400 monostearate and another surface active agent, and may also include a filler. The content of the mixture of surface active agents and the filler in the coating will be determined in each particular case according to the characteristics, e.g. erosion rate and size, of the matrix comprising the active substance.

In addition, the coating may be one which disintegrates or crumbles after erosion of the matrix. A coating of this type would remain intact as long as it was supported by the matrix containing the active substance, but it would lack the ability to remain intact after erosion of the matrix, whereby it would then disintegrate or crumble, so that it would not remain in e.g. a human or animal for any significant amount of time after the complete erosion of the matrix and the release of the active substance.

A composition having the shape of a cylindrical rod may also be prepared without a coating, in which case a substantially or nearly zero order release of the active substance may, for example, be obtained when the active substance is substantially located in the exterior of the composition.

Alternatively, the composition may have the shape of a hollow cylinder or a hollow hemisphere. The term "cylindrical rod" or "hollow cylinder", as used in the context of the present invention, is understood to comprise not only those geometrical forms having a substantially circular cross-section, but also other substantially cylindrical forms, e.g. those having a somewhat flattened cross-section, for example a substantially oval or ellipse shaped cross-section. In addition, other geometrical shapes which allow only a relatively small reduction in the composition's surface area, thereby providing a near zero order release of an active substance substantially homogeneously distributed in the composition, for example a tablet-shaped or slab-shaped composition having a flattened and substantially rectangular or ellipse-shaped cross-section, may also be employed.

It will also be understood by a person skilled in the art that the specific finished form of the composition of the invention may comprise certain minor modifications in order to facilitate the use of the composition in question. For example, a cylindrical rod-shaped composition for delivery of a pharmaceutical powder may have rounded ends so as to avoid possible injury or discomfort when the composition is introduced into the body. In addition, the hollow interior of a composition having the shape of a hollow cylinder may optionally be filled with a readily soluble substance, such as low molecular weight polyethylene glycol, e.g. polyethylene glycol with a molecular weight of about 1500–6000.

As mentioned above, the active substance can be substantially homogeneously dispersed in the crystalline polymer matrix, in which case a substantially zero order release of the active substance is obtained. Alternatively, a pulsatile release of the active substance may be obtained in a composition of the invention which comprises alternating layers. A pulsatile release may thus be obtained with a composition having the above-mentioned shape of a cylindrical rod and comprising alternating substantially transverse layers of a layer comprising the crystalline polymer matrix and the surface active agent, and optionally comprising the active ingredient substantially homogeneously dispersed in the matrix, and a layer comprising the active ingredient, the active ingredient optionally being substantially homogeneously dispersed in the crystalline polymer and the surface active agent. Similarly, a composition in the form of a hollow cylinder may comprise alternating layers of a layer comprising the crystalline polymer matrix and the surface active agent, and optionally comprising the active ingredient substantially homogeneously dispersed in the matrix, and a layer comprising the active ingredient, the active ingredient optionally being substantially homogeneously dispersed in the crystalline polymer and the surface active agent. In a composition comprising alternating layers, the alternating layers may comprise, respectively, two or more different active substances.

These two release patterns (i.e. zero order and pulsatile) may also be combined so that a uniform release of one active substance (for example at a fairly low dosage level) alternates with the release in bursts of the same or another active substance (for example at a higher dosage level).

In another embodiment of the invention, the controlled delivery of an active substance into an aqueous phase is obtained, as mentioned above, with a composition comprising a matrix of room-temperature vulcanizing rubber (RTV rubber) in which particles of a superabsorbent polymer are substantially homogeneously distributed, the superabsorbent polymer particles also being present substantially near the surface of the composition, so that the liquid of the aqueous phase is able to diffuse into the matrix at a limited rate, resulting in swelling of the superabsorbent polymer particles and the localized disruption of the matrix in the vicinity of the swollen particles, whereby the active substance is released. Diffusion of water into the composition according to this embodiment of the invention is also substantially limited to the surface layer, whereby the active substance is released in a specifically controlled manner according to its distribution in the matrix.

The employed RTV rubber typically comprises one or two component RTV silicon elastomers based on polydimethylsiloxane. The matrix of RTV rubber additionally comprises a catalyst and, optionally, a cross-linking agent. Suitable catalysts are stannous octoate or about 0.01–0.1% of a platinum-divinyltetramethyldisiloxane complex containing about 3–3.5% platinum. Suitable cross-linking agents are 0–40% of 1,3-divinyltetramethyldisiloxane, 1,1,3,3-tetramethyldisiloxane or 1,3,5,7-tetramethylcyclotetrasiloxane.

The superabsorbent polymer particles are particles which are able to remain in a semi-solid state upon absorption of water or other liquids, and which are able to absorb at least about 10 times their own weight in water, typically at least about 100 times their own weight in water, especially at least about 200 times their own weight in water. The superabsorbent polymer particles are also able to remain in a semi-solid state upon absorption of bodily fluids, and are able to absorb at least about 5 times their own weight in bodily fluids, typically at least about 20 times their own weight in bodily fluids, especially at least about 40 times their own weight in bodily fluids. Typical superabsorbent polymers which are suitable for use in this embodiment of the invention are polyacrylic acid, modified polyacrylic acid, carboxymethyl cellulose, modified carboxymethyl cellulose and cross-linked polyvinyl pyrrolidone.

The extent of the localized disruption will inter alia be determined by the desired rate of release of the active substance, but it should in any case be sufficient to make other superabsorbent polymer particles accessible to the fluids in question, so as to ensure a progressive disruption of the matrix from the surface inwards at a substantially uniform rate. The amount of superabsorbent polymer to be included in the matrix varies according to the swelling power of the specific superabsorbent polymer selected and the way in which it is arranged in the matrix, but it is suitably present in an amount of about 5–75%, typically about 10–50%, more typically about 20–40% by weight of the matrix.

The active substance included in this embodiment of the invention may be any of the substances mentioned above, i.e. a drug for human or veterinary use, a vitamin or other nutritional supplement, a disinfectant, a deodorant or another substance to be administered continuously in an aqueous environment, and especially a pharmaceutically active powder, e.g. of the type and particle size listed above. The active substance is present in an amount of up to about 60%, typically up to about 50%, by weight of the composition, but it may also be present in much smaller amounts.

The composition according to this embodiment of the invention must also have a geometric shape which enables a substantially constant surface area to become exposed during erosion of the matrix, whereby the desired zero order or pulsatile release of the active substance is obtained according to its distribution in the composition. The specific geometric shape can thus be any of those which are mentioned above.

The active substance in this embodiment of the invention may be substantially homogeneously dispersed in the matrix, in which case a substantially zero order release of the active substance will be obtained. The composition in this embodiment may also comprise alternating layers, in which case a pulsatile release of the active substance will be obtained. A pulsatile release may thus be obtained with a composition according to this embodiment of the invention having the above-described shape of a cylindrical rod and comprising alternating substantially transverse layers of a layer comprising the matrix, and optionally comprising the active ingredient substantially homogeneously dispersed in the matrix, and a layer comprising the active ingredient, the active ingredient optionally being substantially homogeneously distributed in matrix material. Similarly, a composition in the form of a hollow cylinder may comprise alternating longitudinal layers of a layer comprising the matrix, and optionally comprising the active ingredient substantially homogeneously dispersed in the matrix, and a layer comprising the active ingredient, the active ingredient optionally being substantially homogeneously distributed in matrix material.

As explained above, the alternating layers may comprise, respectively, two or more different active substances. The two release patterns (i.e. zero order and pulsarlie) may similarly also be combined in a composition according to this embodiment of the invention, so that a uniform release of one active substance (for example at a fairly low dosage level) alternates with the release in bursts of the same or another active substance (for example at a higher dosage level).

The composition according to either embodiment of the invention may furthermore be used in the preparation of a multiple units pharmaceutical formulation, e.g. in the form of a capsule or tablet. A multiple units pharmaceutical formulation is a formulation which comprises a multiplicity of individual units in such a form that the individual units will be made available upon disintegration of the formulation, typically a capsule or tablet, in the stomach of humans or animals ingesting said formulation. Thus, in this case, at least some of the individual units in said multiple units pharmaceutical formulation will consist of the composition of the invention, the individual units being of a size which allows them to be incorporated into such a formulation.

The composition of the invention may be produced by various methods which are either known per se in the pharmaceutical industry or which, for example, are used in the production of polymer-based materials, depending upon the desired embodiment and the materials employed in the composition in question. As mentioned above, one advantage of the composition according to the invention is that it may be produced by methods which are relatively simple and inexpensive.

A composition without a coating may thus be produced by, for example, extrusion, injection molding or compression molding, while a composition with a coating may be produced by, for example, co-extrusion of the coating with the matrix and the active substance, extrusion and dip coating, injection molding and dip coating, or by extrusion or injection molding and solvent coating by spraying or dipping.

For the preparation of a composition having a matrix of a crystalline polymer, the polymer and the surface active agent will typically be mixed while heating at a temperature sufficient to melt the polymer, and while stirring, so as to obtain a substantially homogeneous mixture. In the case of the active substance being included in the matrix, it may either be added to the molten mixture of the polymer and the surface active agent or it may be added to the mixture prior to heating. The molten mixture is then e.g. extruded or injected, as explained below. For the preparation of a composition for pulsatile release of the active substance, the active substance may conveniently be included in matrix material, the mixture of the active substance and the matrix material being e.g. extruded or injected in layers which alternate with layers of the matrix without the active substance.

For the preparation of a composition having a matrix of RTV rubber, the components of the matrix, i.e. the RTV rubber material, the superabsorbent polymer, and the catalytic accelerator and/or cross-linking agent, are typically mixed together at room temperature while stirring, after which the mixture is e.g. extruded or injected as explained below. The active substance may be added to the mixture prior to e.g. extrusion or injection or it may be e.g. extruded or injected separately, according to the desired characteristics of the composition.

For example, for the production of a composition which has the shape of a cylindrical rod, the matrix material comprising the active substance may be injected into a pre-formed tube. Alternatively, a cylindrical rod-shaped composition may be produced by injecting alternating layers comprising at least, respectively, the matrix material and the active substance into said tube. A cylindrical rod-shaped composition may also be produced by, for example, extruding the matrix material with the active substance dispersed therein, followed by dip coating; or by co-extrusion of a) the matrix material with the active substance dispersed therein and b) the coating.

A cylindrical rod shaped composition may also be produced by injection molding, including two-component or multiple-component injection molding, of the coating and the matrix comprising the active substance. Injection molding is especially suitable for a composition with an trodable coating or a coating which disintegrates or crumbles upon erosion of the matrix, but it is also applicable for other compositions. Typically, a cylinder which functions as a coating is produced in a first step around a core of e.g. iron, after which the matrix is produced in a second step or, alternatively, multiple steps, by injection of the matrix material after removal of the iron core. This method is advantageous in that it is simple and well-suited for mass production.

A composition having the shape of a hollow cylinder may for example be produced by extrusion, compression molding or injection molding. A composition having the shape of a hollow hemisphere may for example be produced by compression molding or by injection molding.

Production methods which involve co-extrusion (for the production of a composition having the shape of cylindrical rod) and extrusion (for the production of a composition having the shape of a hollow cylinder) are especially advantageous, in that they are simple and inexpensive methods for the mass-production of the composition of the invention. The rod or tube which is produced by co-extrusion or extrusion is then cut into smaller segments of an appropriate size. The composition may then be finished, for example by rounding the ends of the individual cylindrical rods or hollow cylinders.

The molten matrix material of compositions based on the use of a crystalline polymer will typically solidify considerably faster than the matrix of a composition based on RTV rubber. Therefore, methods involving extrusion will often be more suitable for compositions comprising a crystalline polymer matrix, while compositions comprising a matrix of RTV rubber will typically more suitably be produced by e.g. injecting the material into pre-formed tubes.

The amount of active substance and the dimensions and specific form of the composition of the invention will of course vary according to the nature of the active substance in question as well as the intended use of the composition. The particular dose to be administered to a person or animal when the composition of the invention is a composition for the delivery of a pharmaceutically active powder will thus depend on such factors as the condition and age of the patient and the particular condition to be treated.

The invention will be more fully described in the following, with reference to the accompanying drawings.

FIG. 1 shows a sectional side view of a coated cylindrical rod-shaped composition for the constant release of an active substance. The composition comprises an active substance which is substantially homogeneously distributed in a matrix 2, and is covered with a coating 1 which is open at one end. The coating 1 is substantially insoluble in and impermeable to fluids such as body fluids during the intended release period. The matrix 2 is thus slowly eroded from the open end by the action of the aqueous medium in which the composition is employed, so that the surface area of the matrix 2 exposed to the aqueous phase remains substantially constant with time, whereby the active substance is released at a constant and strictly controlled rate.

Figure 2:
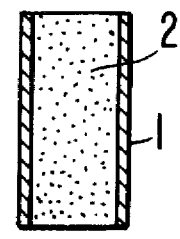
FIG. 2 shows the same composition as FIG. 1, with the exception that the composition is open at both ends, whereby the matrix 2 is eroded towards the center from each of the two open ends.

FIG. 2 shows the same composition as FIG. 1, with the exception that the composition is open at both ends, whereby the matrix 2 is eroded towards the center from each of the two open ends.

Figure 3:
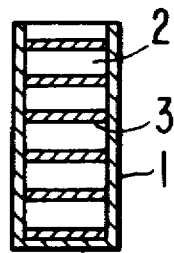
FIG. 3 shows a sectional side view of a coated cylindrical rod-shaped composition for pulsatile release of an active substance.

FIG. 3 shows a sectional side view of a coated cylindrical rod-shaped composition for pulsatile release of an active substance. The composition comprises alternating transverse layers of a matrix 2 and an active substance 3, and is covered with a coating 1 which is open at one end. The coating 1 is substantially insoluble in and impermeable to fluids such as body fluids during the intended release period. The matrix layers 2 are thus slowly eroded from the open end by the action of the aqueous medium in which the composition is employed, thereby releasing the active substance 3 in controlled bursts as each successive layer of the matrix 2 is eroded. Such a composition may also be prepared with an opening in both ends.

Figure 4:
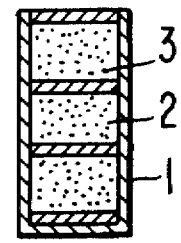
FIG. 4 shows a sectional side view of a composition for the release of two active substances.

FIG. 4 shows a sectional side view of a composition for the release of two active substances. Several transverse layers containing a high concentration of an active substance 3 are arranged in a matrix 2 in which another active substance is uniformly distributed in a lower concentration, the composition being covered with a coating 1 which is substantially insoluble in and impermeable to fluids such as body fluids during the intended release period. The active substance contained in the matrix 2 is released at a substantially uniform rate, and the active substance contained in the layers 3 is released in bursts.

Figure 5:
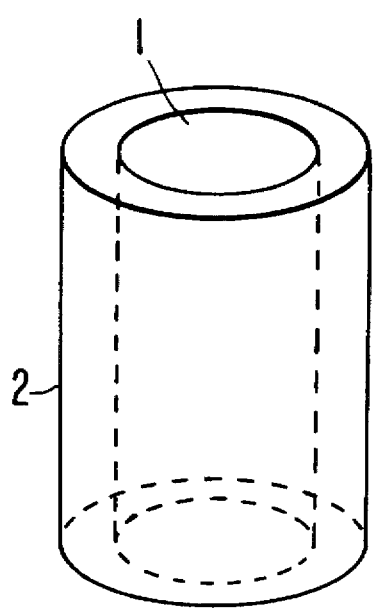
FIG. 5 shows a composition in the shape of a hollow cylinder.

FIG. 5 shows a composition in the shape of a hollow cylinder. In this composition, the active substance is substantially homogeneously distributed in the matrix. The matrix will be eroded both from an interior surface 1 and an exterior surface 2 of the hollow cylinder, so that the surface area exposed to the fluid of the aqueous phase will remain substantially constant with time, whereby a substantially zero order release of the active substance will be obtained.

Figure 6:
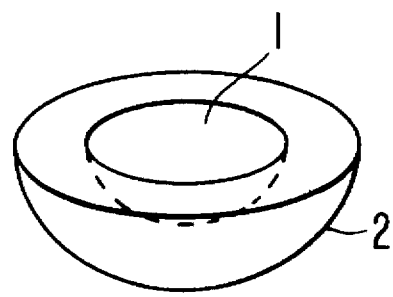
FIG. 6 shows a composition in the shape of a hollow hemisphere, the active substance being substantially homogeneously distributed in the matrix.

FIG. 6 shows a composition in the shape of a hollow hemisphere, the active substance being substantially homogeneously distributed in the matrix. The matrix will be eroded both from an interior surface 1 and an exterior surface 2 of the hollow hemisphere, so that the surface area exposed to the fluid of the aqueous phase will remain substantially constant with time, whereby a substantially zero order release of the active substance will be obtained.

Figure 7:
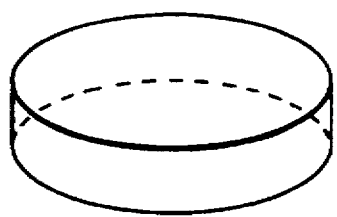
FIG. 7 shows a tablet-shaped composition, the active substance being substantially homogeneously distributed in the matrix.

FIG. 7 shows a tablet-shaped composition, the active substance being substantially homogeneously distributed in the matrix. The matrix will mainly be eroded from the two relatively large flat surfaces, so that the surface area exposed to the fluid of the aqueous phase will remain substantially constant with time, whereby a substantially zero order release of the active substance will be obtained.

Figure 8:
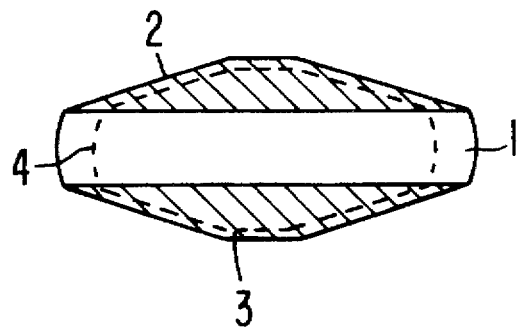
FIG. 8 shows a sectional side view of a cylindrical rod-shaped composition with a coating 2 which erodes at a substantially shlower rate than the matrix 1 comprising the active substance.

FIG. 8 shows a sectional side view of a cylindrical rod-shaped composition with a coating 2 which erodes at a substantially slower rate than the matrix 1 comprising the active substance. After a period of time in a fluid, the matrix 1 will have eroded from each end to 4, while the relatively slowly eroding coating 2 will have eroded to 3.

The invention is further disclosed in the following non-limiting examples.

EXAMPLE 1

Patent Blue was mixed thoroughly with a molten polyethylene glycol (PEG) 20,000 matrix material. The final matrix contained 25% Patent Blue and 75% PEG 20,000. While hot, the matrix was extruded into a pre-formed silicone tube with an internal diameter of 4 mm by means of a syringe and left to cool. The tube was then cut into segments with a length of about 2 cm to leave openings at either end of the dosage form through which release of the active substance may take place. The erosion rate in synthetic urine (1.94% urea, 0.8% $MgSO_4$, 0.11% $CaCl_2$, 97.1% water) was measured over a period of 3 days to be 4 mm/24 h.

EXAMPLE 2

By proceeding in a similar way as described in Example 1, but using a matrix material composed of 90% PEG 20,000 and 10% PEG 400 monostearate with an HLB-value of 11.5, tube segments were prepared containing 75% of the matrix material and 25% Patent Blue. The erosion rate in synthetic urine was measured over a period of 8 days to be a constant 1.3 mm/24 h.

It could be seen in a microscope, using an enlargement of 50–125x, that there was a continuous crystalline phase comprising PEG 20,000, with the PEG 400 monostearate dispersed therein, the latter having been stained with the liposoluble blue colouring and therefore being readily visible. The PEG 400 monostearate was seen to be substantially homogeneously distributed throughout the polymer crystals and at the same time to have filled in and "repaired" cracks and interfaces in and between the crystals.

EXAMPLE 3

10.8 g of PEG 35,000 and 3.6 g of PEG 400 monostearate were mixed while heating at 60°–80° C. until molten. 9.6 g of microcrystalline theophylline were admixed with the molten matrix material until a uniform distribution thereof had been obtained. The molten matrix was extruded into a pre-formed teflon tube with an internal diameter of 6 mm and left to cool. The cooled matrix was then pushed from the tube by means of a piston, and the resulting rod was coated with a 20% solution of polyurethane (Estane 5712 F 30) in acetone. The coated rod was subsequently cut into segments with a length of 20 mm.

The release of theophylline from the resulting dosage forms was measured by immersing the dosage forms in 100 ml (34 g/l) of simulated intestinal juice (Revolyt; composition: 22 mmoles/l of hydrogen carbonate, 15 mmoles/l of potassium, 60 mmoles/l of chloride, 3 mmoles/l of magnesium, 67 mmoles/l of sodium and 3 mmoles/l of sulphate) with constant shaking on an orbital shaker (64 rpm) at 37° C. for 28 hours. Samples were taken every 2 hours and measured by high performance liquid chromatography (HPLC) in a Perkin Elmer HPLC apparatus.

Under these conditions, the release of theophylline was measured to be:

| Release period (hours) | Amount released (μmoles/l) |
|---|---|
| 0–2 | 1380 |
| 2–4 | 1220 |
| 4–6 | 940 |
| 6–22 | 6520 (≈815/2 h) |
| 22–24 | 1055 |
| 24–26 | 850 |
| 26–28 | 810 |

Under the same conditions, the rate of erosion of the matrix was 0.44 mm/h at either end of the dosage form.

EXAMPLE 4

25% of PEG 35,000, 12.5% of PEG 10,000 and 12.5% of PEG 400 monostearate were mixed while heating at 60°–80° C. 49% of gentamycin sulphate (powder) and 1% of tartrazine were added to the molten matrix material until a uniform distribution thereof had been obtained. The molten matrix was extruded into a pre-formed teflon tube with an internal diameter of 5 mm and left to cool. The tube was then cut into segments of 20 mm in length.

The release of gentamycin sulphate from the resulting dosage forms was measured substantially as described in Example 3, except that release was measured spectrophotometrically using a Beckman DU-R spectrophotometer at 430 nm.

The release of gentamycin sulphate was measured over a period of 10 hours to be 10–15 mg/h, and the rate of erosion of the matrix was 1 mm/h.

EXAMPLE 5

36% of PEG 35,000 and 24% of PEG 400 monostearate were mixed while heating at 60°–80° C. 39% of gentamycin sulphate (powder) and 1% of Patent Blue V were added to the molten matrix material until a uniform distribution thereof had been obtained. The molten matrix was extruded into a pre-formed teflon tube with an internal diameter of 5 mm and left to cool. The tube was then cut into segments of 20 mm in length.

The release of gentamycin sulphate from the resulting dosage forms was measured substantially as described in Example 4, except that the release was measured at 638 nm, to be 10–14 mg/h over a period of 8 hours.

EXAMPLE 6

By proceeding in a similar way as described in Example 5, but using PEG 35,000 and PEG 400 monostearate as the matrix material and neomycin sulphate as the active substance, tube segments were prepared containing 33.3% PEG 35,000, 33.3% PEG 400 monostearate, 32.3% neomycin sulphate and 1% tartrazine.

The release of neomycin sulphate from the resulting dosage forms was measured as described in Example 4 to be 8–10 mg/h, and the erosion rate of the matrix was 2 mm/6 h at either end.

EXAMPLE 7

8 g of a block copolymer of ethylene oxide and propylene oxide (Synperonic F-88 from ICI) and 2 g of polyethylene glycol 400 monostearate were mixed while heating at 60°–80° C. until molten. 2 g of Patent Blue V were admixed with the molten matrix material, and the mixture was extruded into a pre-formed teflon tube (diameter 4 mm) and left to cool. The tube was then cut into 20 mm long segments, which were left open at both ends. The erosion rate in synthetic urine was measured to be a constant 1.2 mm/24 h over a period of 8 days.

EXAMPLE 8

0.38 g of D6210 (1,3-divinyltetramethylsiloxane, obtained from Petrarch) was mixed with 4 g of methylhydro-dimethylsiloxane copolymer (PS 123, obtained from Petrarch) at room temperature. To the mixture was added 3 g of Salsorb 84 (a modified polyacrylic acid, particle size 90–850 μm, capacity (in 0.9% NaCl): 45 g/g; obtained from Allied Colloids Ltd.) followed by addition of 4.72 g of erythromycin estolate, 0.4 g of a catalyst solution (0.03% platinum in 10% cyclic vinylmethylsiloxanes and 90% vinyldimethylterminated polydimethylsiloxane) and 1% Patent Blue and thorough mixing. The matrix mixture was extruded into a pre-formed teflon tube with an internal diameter of 6 mm and left to harden for up to 4 hours at room temperature. The tubes were then cut into segments of 20 mm in length.

The release of erythromycin estolate from the resulting dosage forms was measured essentially as described in Example 3 with the exception that the dosage forms were immersed in 100 ml of simulated gastric juice (pepsin-HCl, pH 3) (to which simulated intestinal juice as described above had been added as a buffer).

Using Patent Blue as an indicator, the release was measured to be 9–10 mg/h of erythromycin estolate decreasing to about 7 mg/h over 24 hours. Under the same conditions, the rate of erosion of the matrix was 16.5 mm/24 hours.

EXAMPLE 9

0.19 g of 1,3-divinyltetramethylsiloxane (D6210 from Petrarch) was mixed with 2 g of methylhydro-dimethylsiloxane copolymer (PS123 from Petrarch) at room temperature. To the mixture was added 5 g of carboxy-methylcellulose (A250 from Aqualon), followed by addition of 5 g of gentamycin sulphate and 0.4 g of a catalyst solution (0.03% platinum in 10% cyclic vinylmethylsiloxanes and 90% vinyldimethylterminated polydimethylsiloxane). The matrix was extruded into a pre-formed teflon tube with an internal diameter of 4 mm and left to harden for up to 2 hours at room temperature. The tubes were then cut into segments of 20 mm in length.

The release of gentamycin sulphate in simulated gastric juice was measured as in Example 8 to be 1.3 mg/h. The rate of erosion of the matrix was 6 mm/24 h.

EXAMPLE 10

Comparative examples with various compositions a) A composition containing pure PEG was prepared by extruding molten PEG 10,000 into a pre-formed teflon tube (diameter 4 mm). After cooling, the matrix was pushed from the tube by means of a piston, and the resulting rod was coated with a 20% solution of polyurethane (Estane 5712 F 30) in acetone. The coated rod was subsequently cut into segments having a length of 10 mm. The erosion rate of the PEG in simulated intestinal juice (Example 3) was 4 mm/h.

b) A composition was prepared and the erosion rate measured as in a) above, with the exception that the PEG was PEG 35,000. The erosion rate was 1.8 mm/h.

c) A mixture of 95% PEG 35,000 and 5% PEG 400 monostearate was melted and a coated rod was prepared as in a) above, using pre-formed teflon tubes with a diameter of 6 mm. The erosion rate in simulated intestinal juice was measured to be 1.45 mm/h.

d) A mixture of 75% PEG 35,000 and 25% PEG 400 monostearate was melted. Dextrin was added as a filler in an amount of 40% of the total weight of the composition. The resulting mixture was extruded into pre-formed teflon tubes (diameter 10 mm) and coated rods were prepared as in a) above. The erosion rate in simulated intestinal juice was measured to be 0.34 mm/h.

e) A mixture of 75% PEG 35,000 and 25% PEG 400 monostearate was melted. To the molten mixture was added a mixture of dextrin as a filler and morphine hydrochloride as an active substance, the amount of dextrin and morphine hydrochloride being 40% of the total weight of the composition. The composition, which contained 3.55% morphine hydrochloride, was extruded into pre-formed teflon tubes (diameter 6 mm). The rods were coated as in a) and cut into 10 mm segments. The release of morphine hydrochloride in simulated intestinal juice was measured by HPLC to be 1 mg/h over a period of 10 hours, and the erosion rate was measured to be 0.43 mm/h.

f) A composition was prepared as in e) above, with the exception that the content of morphine hydrochloride was 9.54%. Release of morphine hydrochloride in simulated intestinal juice was measured by HPLC to be 3 mg/h over a period of 10 hours, and the erosion rate was measured to be 0.48 mm/h.

g) A mixture of 75% PEG 35,000 and 25% PEG 400 monostearate was melted and mixed with tartrazine in an amount of 3.55%. The mixture was extruded into pre-formed teflon tubes (diameter 6 mm), coated as in a) and cut into 12 mm segments. The erosion rate in simulated intestinal juice was measured to be a constant 1.5 mm/h from each end over a period of 4 hours.

h) 10.5 g of PEG 35,000 and 3.5 g PEG 400 monostearate were melted and mixed together. 6.0 g of methotrexate was added, resulting in a mixture comprising 52.2% PEG 35,000, 17.5% PEG 400 monostearate and 30% methotrexate (MTX). The molten mixture was extruded into pre-formed teflon tubes (diameter 4 mm), and coated rods were prepared as in a). Release of MTX in synthetic urine (Example 1) was measured by HPLC to be a constant 1.5 mg/h over a period of 10 hours, and the erosion rate was 0.5 mm/h.

i) 5.4 g of PEG 35,000 and 1.8 g PEG 400 monostearate were melted and mixed with 4.8 g of dextrin/tartrazine (99:1). The mixture was extruded into pre-formed teflon tubes (diameter 6 mm) and coated as in a). Erosion in simulated intestinal juice was measured with a spectrophotometer at a wavelength of 430 nm to be 0.34 mm/h over a period of 12 hours.

j) 1 g of PEG 35,000, 0.5 g of PEG 400 monostearate and 1 g of a diacetylated tartaric acid ester of mono- and diglycerides (Dat-S from Grindsted Products, Denmark) were melted together. 2.5 g of sucralfate was then added and the mixture was extruded into pre-formed teflon tubes (diameter 6 mm). Erosion in simulated intestinal juice was measured to be 1 mm in 8 hours.

k) A composition similar to that of j) was prepared, but without the diacetylated tartaric acid ester. 4 g of PEG 35,000 and 2 g of PEG 400 monostearate were melted, and 4 g of sucralfate was added to the molten mixture. The mixture was extruded into pre-formed teflon tubes (diameter 6 mm) and coated as in a). Erosion in simulated intestinal juice was greater than 2 mm in 8 hours.

l) 5 g of PEG 35,000 were melted and extruded into a pre-formed teflon tube (diameter 6 mm). One end of the tube was dipped in molten PEG 1500 containing 10% tartrazine. The composition was removed from the tube and coated with Estane F30, the end which had been dipped in the mixture of PEG 1500 and tartrazine also being coated. The composition was then cut to a length of 7.5 mm. Erosion in simulated intestinal juice resulted in a yellow colouration of the liquid after 4 hours, which showed that the erosion rate was about 1.9 mm/h.

m) 2.25 g of PEG 35,000 and 0.75 g of PEG 400 monostearate were melted, 2 g of dextrin was added (40% dextrin), and the mixture was extruded into a preformed teflon tube (diameter 6 mm). Following the procedure of l) above, 3.5 mm long coated rods with PEG 1500+tartrazine at the coated end were prepared and subsequently eroded in simulated intestinal juice. Yellow colouration was seen after 8 hours, which showed that the erosion rate was about 0.23 mm/h.

EXAMPLE 11

A composition was prepared as described in Example 3, with the exception that the rods were cut into segments having a length of 12 mm. The resulting rods contained 195 mg PEG 35,000, 65 mg PEG 400 monostearate and 170 mg microcrystalline theophylline. The in vitro erosion rate, measured as described in Example 3, was determined to be 1 mm/h, corresponding to approximately 15 mg theophylline released per hour. The exact amount of theophylline released, as determined by HPLC, was as follows:

| Release period (hours) | Amount released ($\mu$moles/l) |
| --- | --- |
| 0–2 | 2575 |
| 2–4 | 1740 |
| 4–6 | 1645 |
| 6–8 | 1740 |

The in vivo release of theophylline from this composition was tested in six patients, 3 males and 3 females, aged 18–42 years (mean age 30 years), weighing from 63 to 85 kg (mean weight 66 kg), all of whom were diagnosed as having bronchial asthma.

The first dose was given to the patients before breakfast (i.e. in the fasting state) as two units of the composition (340 mg theophylline) together with 100 ml of liquid. The second dose was given at least three days later in the morning as an i.v. injection of theophylline (Theo-Dur 20 mg/ml) over a period of 10 minutes, in a dose of 5 mg/kg ideal body weight, in order to determine the serumhalf-life of theophylline in the individual patients. Following the oral dose, venous blood samples were drawn at 0, 1, 2, 3, 4, 6, 8, 10, 12, 14, 16 and 24 hours. Serum samples were drawn at 0, 15 min., 30 min., 60 min., 90 min., and 2, 3, 5, 7, 9 and 11 hours after the i.v. dose. The serum portion of the blood specimen was immediately frozen at −20° C. and kept frozen until analyzed 2 weeks later. The amount of theophylline in the serum was assayed by HPLC with an accuracy of ±5%. The measured serum levels together with the calculated serum half-life of theophylline in the individual patients are shown in the following table:

| Patient No. | Serum half-life (hours) | Theophyllin in serum (μmoles/l) Hours | | | | | | | | | |
|---|---|---|---|---|---|---|---|---|---|---|---|
| | | 1 | 2 | 3 | 4 | 6 | 8 | 10 | 12 | 14 | 16 | 24 |
| 1 | 6 | 21 | 21 | — | 22 | 21 | 20 | 17 | 16 | 14 | 11 | 9 |
| 2 | 9 | 7 | 16 | 24 | 30 | 36 | 32 | 30 | 32 | 30 | 25 | 19 |
| 3 | 8 | 25 | 38 | 39 | 39 | 39 | 44 | 51 | 50 | 45 | 41 | 30 |
| 4 | 9 | 11 | 19 | 22 | 26 | 39 | 33 | 29 | 26 | 21 | 19 | 15 |
| 5 | 7 | 9 | 14 | 19 | 20 | 25 | 21 | 19 | 22 | 16 | 14 | 8 |
| 6 | 8 | 9 | 21 | 19 | 18 | 20 | 21 | 21 | 22 | 26 | 25 | 18 |

EXAMPLE 12

The in vivo release of morphine hydrochloride from the composition of Example 10 e) was tested in two individuals, both healthy males aged 40 years, weighing 85 kg (patient 1) and 65 kg (patient 2). The composition, which contained 10 mg of morphine hydrochloride, was taken together with 100 ml of liquid two hours after breakfast. Concentrations of morphine hydrochloride in serum were determined every second hour by drawing venous blood samples, which were then kept cold until the next day, when the serum portion was separated and frozen at −20° C. The concentration of morphine hydrochloride in the serum was analyzed three weeks later by using a RIAS method, which determines both free and conjugated morphine hydrochloride with an accuracy of ±5% and with a sensitivity of 2 ng total morphine hydrochloride/ml serum. The following concentrations of morphine hydrochloride in serum were found:

| | Morphine hydrochloride in serum (ng/ml) Hours: | | | | | | | | |
|---|---|---|---|---|---|---|---|---|---|
| | 1 | 2 | 4 | 6 | 8 | 10 | 12 | 14 | 21 |
| Patient 1 | 18 | 32 | 44 | 46 | 42 | 51 | 76 | 60 | 34 |
| Patient 2 | 35 | 76 | 64 | 44 | 31 | 21 | 27 | — | ... |

EXAMPLE 13

18% of PEG 20,000, 27% of PEG 35,000 and 15% of PEG 400 monostearate were mixed while heating at 65°–75° C., and 40% of gentamycin sulphate was added to the molten matrix material and mixed until uniformly distributed. The molten mixture was extruded into a pre-formed teflon tube (diameter 4 mm) and left to cool. The resulting rod was then pushed from the tube by means of a piston and the rod was cut into pieces with a length of 15 or 30 mm and dip-coated with a 20% solution of Estane 30, leaving one end uncoated. The release of gentamycin sulphate from the resulting composition was measured in vitro substantially as described in Example 3, and by using a biological agar hole diffusion method for the assaying of gentamycin sulphate. A release of gentamycin sulphate of 14 mg/72 hours was found.

The erosion rate from the open end of the composition was measured to be 1 mm/24 hours, corresponding to a release of 5 mg of gentamycin sulphate/24 hours.

The composition as described above was glued on the tip of a urinary balloon catheter (Ruch, ZF, 5 ml, size 12). The diameter of the tip was similar to that of the catheter, and the length of the composition was 30 mm.

The in vivo release was examined in an animal model. A female pig, SPR Danish landrace x Yorkshire LYY, weighing 22 kg, was used. The pig was housed in a wire mesh cage with a stainless steel tray for collection of urine. The catheter was introduced into the urine bladder while the pig was anesthetized with Sedaperone (i.m.) and Hypnodil (j.p.). Atropine (i.m.) was given at the time to prevent salivation. 20 ml aliquots of urine were collected from the tray every 24 hours and the concentration of gentamycin sulphate in the urine was determined by using a biological agar hole diffusion method with a sensitivity of 0.2 μg gentamycin sulphate/mg urine. The following concentrations of gentamycin sulphate were found:

| | μg gentamycin sulphate/ ml urine |
|---|---|
| 0–24 hours: | 1.75 |
| 24–48 hours: | 1.40 |
| 48–72 hours: | 1.55 |

At autopsy on day 4 there was a slight haemorrhage on the outside of the bladder. The mucosa of the bladder and urethra were found to be normal.

EXAMPLE 14

An animal study using a pig as described above (Example 13) was repeated using the same composition. In this study, an Argyle silicone balloon catheter (12 ch, 5 ml, lot No. 027603) was used. Each catheter was equipped with a cylindrical 15 mm long composition, and the diameter of the tip was similar to that of the catheter. The study lasted for a period of 7 days. Two pigs (weighing 20 and 21 kg) were used. The following concentrations of gentamycin sulphate were found:

| Day after catheter insertion | μg gentamycin sulphate/ml urine | |
|---|---|---|
| | Pig 1 | Pig 2 |
| 1 | 2.9 | 1.25 |
| 2 | 4.7 | 0.25 |
| 3 | 4.6 | 0.95 |
| 4 | 3.4 | 0.27 |
| 5 | 5.3 | 0.59 |
| 6 | — | 1.25 |
| 7 | ... | 3.40 |

The release of gentamycin sulphate from the device was probably blocked in pig 1 from day 5, since the composition was only half-emptied when the catheter was removed on day 7.

At autopsy on day 8 there were signs of mucosal tissue irritation in the trigonum area of pig 1, which was probably caused by the presence of the tip of the catheter in the bladder. The bladder mucosa and urethral mucosa were found to be normal in pig 2.

We claim:

1. A composition for the controlled delivery of an active substance into an aqueous phase, the composition comprising:
   a matrix comprising a crystalline polyethylene glycol polymer, and
   a non-ionic emulsifier dispersed in the matrix in an amount of between about 2% and about 50% by weight of the crystalline polyethylene glycol polymer and the non-ionic emulsifier, the non-ionic emulsifier having at least one domain which is compatible with the crystalline polyethylene glycol polymer and being selected from the group consisting of a fatty acid ester and a fatty alcohol ether,
   the active substance being dispersed in the matrix, whereby the active substance is delivered into the aqueous phase by erosion of a surface of the composition at an approximately constant and pH-independent rate,
   wherein the non-ionic emulsifier has an HLB value in the range of from about 4 to about 16, and
   wherein the matrix retains approximately its geometric shape during erosion of its surface.

2. The composition according to claim 1 comprising a filler dispersed in the matrix.

3. The composition according to claim 1 wherein the active substance is an active substance substantially homogeneously dispersed therein.

4. The composition according to claim 1, wherein the polyethylene glycol has a molecular weight of between about 20,000 daltons and about 500,000 daltons.

5. The composition according to claim 1, wherein the polyethylene glycol has a molecular weight of between about 20,000 daltons and about 100,000 daltons.

6. The composition according to claim 1, wherein the polyethylene glycol has a molecular weight of between about 20,000 daltons and about 50,000 daltons.

7. The composition according to claim 1, wherein the polyethylene glycol has a molecular weight of between about 20,000 daltons and about 35,000 daltons.

8. The composition according to claim 1 wherein the polyethylene glycol has a molecular weight of about 35,000 daltons.

9. The composition according to claim 1 wherein the polyethylene glycol has a molecular weight of about 50,000 daltons.

10. The composition according to claim 1 wherein the polyethylene glycol has a molecular weight of about 100,000 daltons.

11. The composition according to claim 1 wherein the polyethylene glycol has a molecular weight of about 500,000 daltons.

12. A composition according to claim 1, wherein the active substance is selected from the group consisting of a drug for animal use, a nutritional supplement, a disinfectant and a deodorant.

13. The composition according to claim 12, wherein the nutritional supplement is a micronutrient.

14. The composition according to claim 1, wherein the active substance is present in an amount of up to about 60% by weight of the composition.

15. The composition according to claim 1, wherein or the fatty acid ester and the fatty alcohol ether, whichever applies, comprises a carbon chain of between 12 and 24 carbon atoms.

16. The composition according to claim 1, wherein the non-ionic emulsifier is selected from the group consisting of an ester of palmitic acid, an ester of stearic acid, an ether of palmityl alcohol, an ether of stearyl alcohol, and combinations thereof.

17. The composition according to claim 1, wherein the non-ionic emulsifier is selected from the group consisting of a polyglycol ester, a polyglycol ether, a sugar ester, and a sugar ether.

18. The composition according to claim 1, wherein the non-ionic emulsifier is selected from the group consisting of a polyethylene glycol ester, a polyethylene glycol ether, a sorbitan ester, a sorbitan ether and combinations thereof.

19. The composition according to claim 1, wherein the non-ionic emulsifier comprises a polyethylene glycol stearate.

20. The composition according to claim 1, comprising a filler dispersed in the matrix, wherein the filler is selected from the group consisting of dextrin, sucralfate, calcium hydroxyl-apatite, calcium phosphate, and a fatty acid salt.

21. The composition according to claim 1, comprising a filler dispersed in the matrix, wherein a combination of the filler and the active substance comprises up to about 60% by weight of the composition.

22. The composition according to claim 1, wherein the composition defines a geometric shape whereby a substantiality constant area of the first matrix is exposed which enables a substantially constant surface area of the matrix to be exposed during erosion of the matrix.

23. The composition according to claim 1, wherein the active substance is selected from the group consisting of an antimicrobial, an antifungal, an antiparasitic, an antiviral, an antineoplastic, a cytostatic, an analgesic, an antiinflammatory, an anticonvulsant, a muscle relaxant, an antiemetic, an antidepressant, a tranquilizer, a hypnotic, a sedative, a CNS-stimulating agent, ergot, a gastrointestinal agent, an uricosuric, a sympathomimetic, an anticholinergic, a dopaminergic, a parasympathomimetic, a coagulation modifying agent, an enzyme, a vaccine, an antibody, an electrolyte, a micronutrient, a macronutrient, a contrast material, a radiopharmaceutical, a diuretic, an antihypertensive, a vasodilator, a β-blocker, an antiarrhythmic, a cardiac glycoside, a hormone, an antihormone, a contraceptive, an antidiabetic and an antiallergic.

24. The composition according to claim 23, wherein the polypeptide is an antibody.

25. The composition of claim 1, wherein the crystalline polyethylene glycol polymer has a molecular weight of at least about 20,000 daltons.

26. The composition of claim 1, wherein the non-ionic emulsifier has an HLB value in the range of from about 6 to about 16.

27. The composition of claim 1, wherein the non-ionic emulsifier has an HLB value in the range of from about 6 to about 14.

28. The composition of claim 1, wherein the non-ionic emulsifier has an HLB value in the range of from about 8 to about 14.

29. The composition of claim 1, wherein the non-ionic emulsifier has an HLB value in the range of from about 8 to about 12.

30. The composition according to claim 1, wherein the active substance is an antimicrobial substance selected from antifungals and antivirals.

31. The composition according to claim 1, wherein said enzyme comprises one or more polypeptides.

32. A method of preparing a composition for the controlled delivery of an active substance into an aqueous phase, the method comprising the steps of:
forming a matrix comprising a crystalline polyethylene glycol polymer,
dispersing a non-ionic emulsifier in the matrix in an amount of between about 2% and about 50% by weight of the crystalline polyethylene glycol polymer and the non-ionic emulsifier, the non-ionic emulsifier having at least one domain which is compatible with the crystalline polyethylene glycol polymer and being selected from the group consisting of a fatty acid ester and a fatty acid alcohol ether, and
dispersing the active substance in the matrix, whereby the active substance is delivered into the aqueous phase by the erosion of a surface of the composition at an approximately constant and pH-independent rate,
wherein the non-ionic emulsifier has an HLB value in the range of from about 4 to about 16.

33. The method according to claim 32, further comprising the step of shaping the composition by injection molding.

34. The method according to claim 32, further comprising the step of shaping the composition by compression molding.

35. The method according to claim 32, wherein the polyethylene glycol has a molecular weight of between about 20,000 daltons and about 500,000 daltons.

36. The method according to claim 32, wherein the polyethylene glycol has a molecular weight of between about 20,000 daltons and about 100,000 daltons.

37. The method according to claim 32, wherein the polyethylene glycol has a molecular weight of between about 20,000 daltons and about 50,000 daltons.

38. The method according to claim 23, wherein the polyethylene glycol has a molecular weight of between about 20,000 daltons and about 35,000 daltons.

39. The method according to claim 32, wherein the polyethylene glycol has a molecular weight of about 35,000 daltons.

40. The method according to claim 32, wherein the polyethylene glycol has a molecular weight of about 50,000 daltons.

41. The method according to claim 32, wherein the polyethylene glycol has a molecular weight of about 100,000 daltons.

42. The method according to claim 32 wherein the polyethylene glycol has a molecular weight of about 500,000 daltons.

43. The method according to claim 32, wherein the active substance is selected from the group consisting of a drug for human or veterinary use, a nutritional supplement, a disinfectant and a deodorant.

44. The method according to claim 32, wherein the active substance is present in an amount of up to 60%, by weight of the composition.

45. The method according to claim 32, wherein at least one of the fatty acid ester and the fatty alcohol ether comprises a carbon chain of between 12 and 24 carbon atoms.

46. The method according to claim 32, wherein the non-ionic emulsifier is selected from the group consisting of an ester of palmitic acid, an ester of stearic acid, an ether of palmityl alcohol, an ether of stearyl alcohol, and combinations thereof.

47. The method according to claim 32, wherein the non-ionic emulsifier is selected from the group consisting of a polyglycol ester, a polyglycol ether, a sugar ester and a sugar ether.

48. The method according to claim 32, wherein the non-ionic emulsifier is selected from the group consisting of a polyethylene glycol ester, a polyethylene glycol ether, a sorbitan ester, a sorbitan ether, and combinations thereof.

49. The method according to claim 32, wherein the non-ionic emulsifier comprises polyethylene glycol monostearate, including polyethylene glycol 400 monostearate.

50. The method according to claim 32, comprising the step of dispersing a filler in the matrix, wherein the filler is selected from the group consisting of dextrin, sucralfate, calcium hydroxyl-apatite, calcium phosphate, and a fatty acid salt.

51. The method according to claim 32, comprising the step of dispersing a filler in the matrix, wherein a combination of the filler and the active substance comprises up to about 60% by weight of the composition.

52. The method according to claim 32, comprising the step of forming the composition into a geometric shape which enables an approximately constant surface area of the matrix to be exposed during erosion of the matrix.

53. The method according to claim 32, comprising the step of substantially homogeneously dispersing the active substance in the crystalline polymer matrix.

54. The method according to claim 32, comprising the step of dispersing a filler in the matrix.

55. A composition for the controlled delivery of an active substance into an aqueous phase, the composition comprising:
a matrix comprising a crystalline polyethylene glycol polymer having a molecular weight of at least about 35,000 daltons, and
a non-ionic emulsifier dispersed in the matrix in an amount of between about 2% and about 50% by weight of the crystalline polyethylene glycol polymer and the non-ionic emulsifier, the non-ionic emulsifier having at least one domain which is compatible with the crystalline polyethylene glycol polymer and being selected from the group consisting of a fatty acid ester and a fatty alcohol ether,
the active substance being dispersed in the matrix, whereby the active substance is delivered into the aqueous phase by erosion of a surface of the composition at an approximately constant and pH-independent rate,
wherein the non-ionic emulsifier has an HLB value in the range of from about 4 to about 16, and
wherein the matrix retains approximately its geometric shape during erosion of its surface.

56. The composition of claim 55 wherein the polyethylene glycol has a molecular weight of at least about 50,000 daltons.

57. The composition of claim 55 wherein the polyethylene glycol has a molecular weight of at least about 100,000 daltons.

58. The composition of claim 55 wherein the polyethylene glycol has a molecular weight of at least about 500,000 daltons.

59. The composition of claim 55 wherein the non-ionic emulsifier comprises a polyethylene glycol stearate.

60. A composition for the controlled delivery of an active substance into an aqueous phase, the composition comprising:
a matrix comprising a crystalline polyethylene glycol polymer having a molecular weight of at least about 21,000 daltons, and a non-ionic emulsifier dispersed in the matrix in an amount of between about 2% and about 50% by weight of the crystalline polyethylene glycol polymer and the non-ionic emulsifier, the non-ionic emulsifier having at least one domain which is compatible with the crystalline polyethylene glycol polymer and being selected from the group consisting of a fatty acid ester and a fatty alcohol ether, the active substance being dispersed in the matrix, whereby the active substance is delivered into the aqueous phase by erosion of a surface of the composition at an approximately constant and Ph-independent rate, wherein the non-ionic emulsifier has an HLB value in the range of from about 4 to about 16, and wherein the matrix retains approximately its geometric shape during erosion of its surface.

* * * * *

UNITED STATES PATENT AND TRADEMARK OFFICE
CERTIFICATE OF CORRECTION

PATENT NO. : 5,618,560
DATED : April 8, 1997
INVENTOR(S) : BAR-SHALOM et al.

It is certified that error appears in the above-identified patent and that said Letters Patent is hereby corrected as shown below:

Claim 10, col. 21, line 2, delete "100,"
                             line 3, delete "000" and insert --100,000--.

Claim 11, col. 21, line 2, delete "500,"
                             line 3, delete "000" and insert --500,000--.

Claim 41, col. 23, line 2, delete "100,"
                             line 3, delete "000" and insert --100,000--.

Signed and Sealed this

Thirteenth Day of January, 1998

Attest:

BRUCE LEHMAN

Attesting Officer

Commissioner of Patents and Trademarks